(12) United States Patent
Favreau et al.

(10) Patent No.: US 11,612,390 B2
(45) Date of Patent: Mar. 28, 2023

(54) SUTURING CLOSURE SCOPE WITH ALTERNATIVE NEEDLE ORIENTATION

(71) Applicant: Boston Scientific Scimed, Inc., Maple Grove, MN (US)

(72) Inventors: John T. Favreau, Spencer, MA (US); Ethan Miller, Ashland, MA (US); Peter L. Dayton, Brookline, MA (US); Shawn Ryan, Littleton, MA (US); Morgan Zhu, Somerville, MA (US); Shaun D. Comee, Fiskdale, MA (US); James J. Scutti, Arlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 392 days.

(21) Appl. No.: 17/010,075

(22) Filed: Sep. 2, 2020

(65) Prior Publication Data
US 2021/0068812 A1    Mar. 11, 2021

Related U.S. Application Data

(60) Provisional application No. 62/896,998, filed on Sep. 6, 2019.

(51) Int. Cl.
| | |
|---|---|
| *A61B 17/04* | (2006.01) |
| *A61B 1/05* | (2006.01) |
| *A61B 1/06* | (2006.01) |
| *A61B 17/00* | (2006.01) |

(52) U.S. Cl.
CPC .......... *A61B 17/0469* (2013.01); *A61B 1/05* (2013.01); *A61B 1/0661* (2013.01); *A61B 2017/0023* (2013.01)

(58) Field of Classification Search
CPC ........ A61B 17/0469; A61B 2017/0023; A61B 1/05; A61B 1/0661
See application file for complete search history.

(56) References Cited

U.S. PATENT DOCUMENTS

| | | | | |
|---|---|---|---|---|
| 5,709,694 A | * | 1/1998 | Greenberg .......... | A61B 17/0483 606/147 |
| 5,954,733 A | * | 9/1999 | Yoon .................. | A61B 18/1445 606/147 |
| 5,984,932 A | * | 11/1999 | Yoon .................. | A61B 17/0469 606/147 |
| 5,993,466 A | * | 11/1999 | Yoon .................. | A61B 18/1445 606/147 |
| 6,086,601 A | * | 7/2000 | Yoon .................... | A61B 17/062 606/147 |
| 6,159,224 A | * | 12/2000 | Yoon .................. | A61B 18/1445 606/147 |

(Continued)

FOREIGN PATENT DOCUMENTS

WO    2018046822 A1    3/2018

OTHER PUBLICATIONS

International Search Report and Written Opinion for the International Patent Application No. PCT/US2020/048995, dated Dec. 10, 2020, 16 pages.

*Primary Examiner* — Phong Son H Dang
(74) *Attorney, Agent, or Firm* — Seager, Tufte & Wickhem, LLP

(57) ABSTRACT

The present disclosure relates generally to the field of medical devices. In particular, the present disclosure relates to single-use endoscopic medical devices with integrated and purpose-built functionality.

7 Claims, 6 Drawing Sheets

(56) References Cited

U.S. PATENT DOCUMENTS

| | | | |
|---|---|---|---|
| 9,427,226 B2* | 8/2016 | Martin | A61B 17/0482 |
| 9,649,107 B2* | 5/2017 | Brecher | A61B 17/06066 |
| 9,675,339 B2* | 6/2017 | Brecher | A61B 17/0469 |
| 9,867,608 B1* | 1/2018 | Shelton, IV | A61B 17/0469 |
| 10,595,855 B2* | 3/2020 | Malkowski | A61B 17/0469 |
| 10,939,909 B2* | 3/2021 | Zeiner | A61B 17/06114 |
| 2002/0120290 A1 | 8/2002 | Green | |
| 2010/0081875 A1 | 4/2010 | Fowler et al. | |
| 2011/0152891 A1 | 6/2011 | McLawhorn et al. | |
| 2011/0313433 A1* | 12/2011 | Woodard, Jr. | A61B 17/0469 606/145 |

* cited by examiner

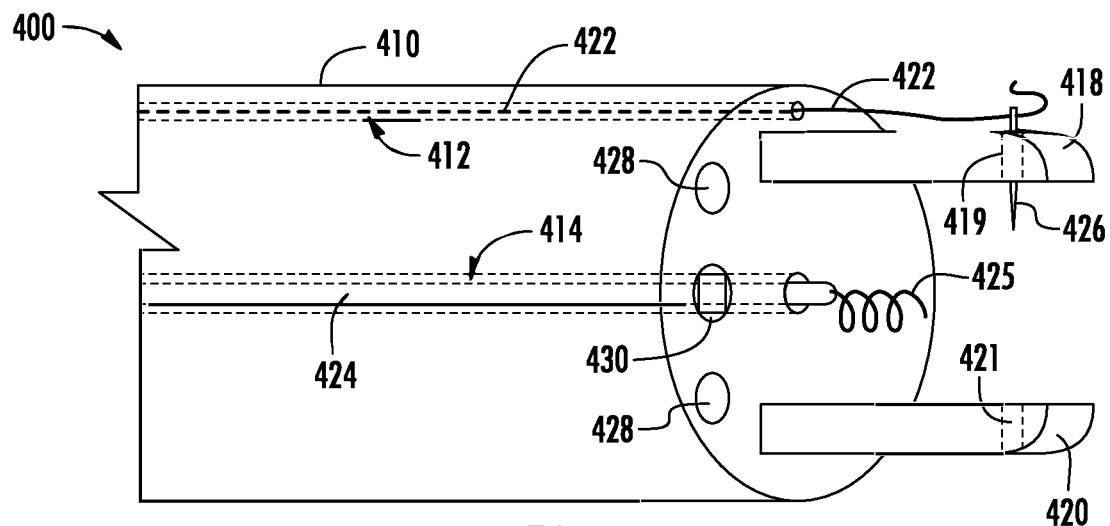
FIG. 5A
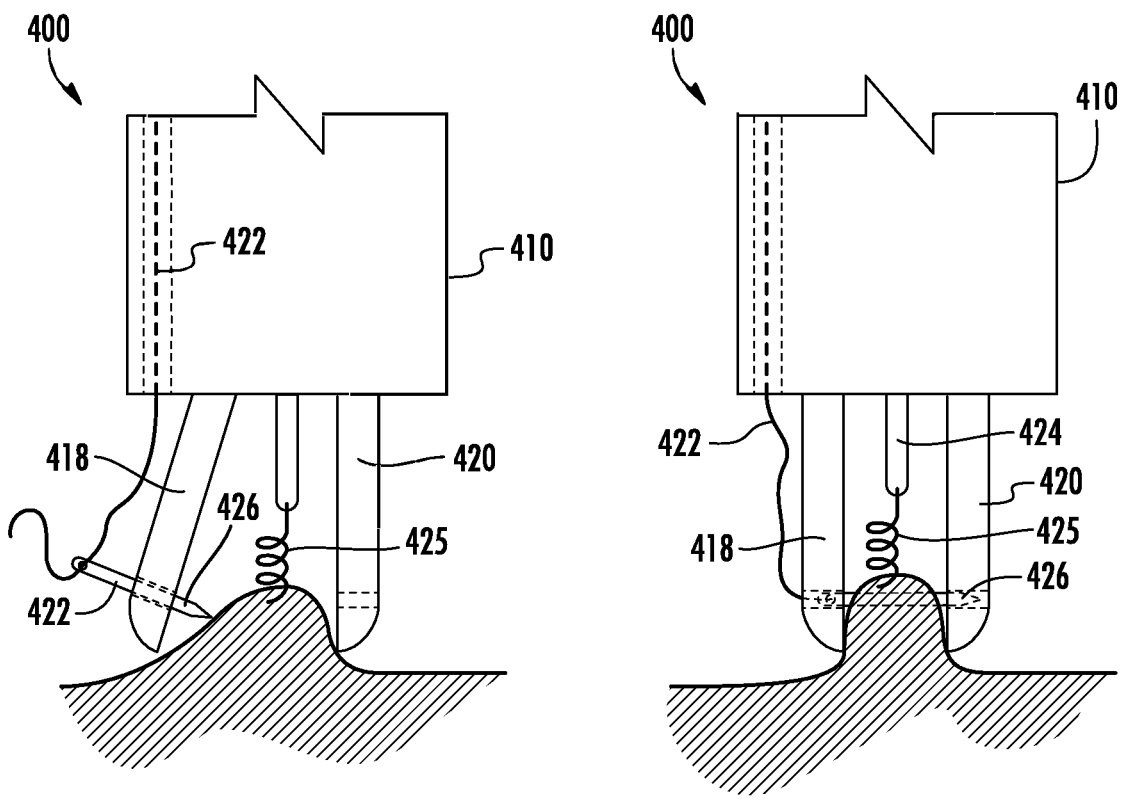
FIG. 5B  FIG. 5C

SUTURING CLOSURE SCOPE WITH ALTERNATIVE NEEDLE ORIENTATION

PRIORITY

This application claims the benefit of priority under 35 USC § 119 to U.S. Provisional Patent Application Ser. No. 62/896,998, filed Sep. 6, 2019, which is incorporated by reference herein in its entirety and for all purposes.

FIELD

The present disclosure relates generally to the field of medical devices. In particular, the present disclosure relates to endoscopic medical devices with integrated and purpose-built functionality.

BACKGROUND

Multi-purpose endoscopes include one or more working channels to support a variety of medical instruments designed to perform a specific/dedicated function under direct visualization. Due at least in part to their multi-purpose functionality, these endoscopes tend to be somewhat large/bulky and lack an intrinsic (e.g., purpose-built) ability to treat and/or manipulate tissues independent of the specific medical instrument inserted through their working channel(s). For example, the functionality (e.g., visibility, maneuverability, etc.) of some currently available endoscopic suturing devices designed for use with multi-purpose endoscopes is inherently limited by the requirement that they fit within the limited/standard dimensions of the working channel(s).

A variety of advantageous medical outcomes may therefore be realized by the endoscopic medical devices of the present disclosure.

SUMMARY

In one aspect, the present disclosure relates to an endoscopic medical device comprising an elongate member. The elongate member may define a suture channel and a working channel therethrough. An elongate sheath may be rotatably disposed about the elongate member. A needle passer may extend from a distal end of the elongate sheath. A needle grasper may extend from a distal end of the elongate member. The elongate sheath may be configured to rotate about the elongate member between a first position, a second position and a third position. In the first position, the needle passer may be disposed substantially opposite the needle grasper. In the second position, a first side of the needle passer may be substantially adjacent to a first side of the needle grasper. In the third position, a second side of the needle passer may be substantially adjacent to a second side of the needle grasper.

In the above-described and other embodiments, a suture may be movably disposed within the suture channel and a medical accessory device may be movably disposed within the working channel. A distal end of the suture may be attached to a curved needle. A distal end of the medical accessory device may be configured to extend beyond the distal end of the elongate member to engage a target tissue. In the first position the curved needle may be releasably attached to the needle passer. In the second position the curved needle may be transferred from the needle passer to the needle grasper. In the third position the curved needle may be transferred from the needle grasper to the needle passer. A camera may be disposed on the distal end of the elongate member. A light source may be disposed on the distal end of the elongate member.

In another aspect, the present disclosure relates to a medical device comprising an endoscope. The endoscope may define a suture channel and a working channel therethrough. A working space may be formed within a distal portion of the endoscope. A distal end of the suture channel may open into a first side of the working space. A distal end of the working channel may open into a third side of the working space. A needle passer may be movably disposed within the distal portion of the endoscope. The needle passer may be configured to move between a first position on the first side of the working space and a second position on a second side of the working space.

In the above-described and other embodiments, a suture may be movably disposed within the suture channel and a medical accessory device may be movably disposed within the working channel. A distal end of the suture may be attached to a needle. A distal end of the medical accessory device may be configured to extend into the working space to engage a target tissue. A needle receiver may be disposed within the second side of the working space and configured to receive the needle passer. A camera may be disposed on the third side of the working space. A light source may be disposed on the third side of the working space.

In yet another aspect, the present disclosure relates to an endoscopic medical device comprising an elongate member. A suturing arm may extend from a distal end of the elongate member. The suturing arm may include first and second projections defining a working space therebetween. A suture channel may extend through the elongate member and through a first projection of the suturing arm. A working channel may extend through the elongate member and through a portion of the suturing arm between the first and second projections. A curved needle passer may be movably disposed within the suturing arm. The curved needle passer may be configured to rotate within the suturing arm between a first position and a second position.

In the above-described and other embodiments, a suture may be movably disposed within the suture channel and a medical accessory device may be movably disposed within the working channel. A distal end of the suture may be attached to a curved needle. A distal end of the medical accessory device may be configured to extend beyond a distal end of the first and second projections to engage a target tissue. The curved needle passer may be disposed within the first projection of the suturing arm when in the first position. The curved needle passer may be disposed within the second projection of the suturing arm when in the second position. A camera may be disposed on the distal end of the elongate member.

In yet another aspect, the present disclosure relates to an endoscopic medical device comprising an elongate member. The elongate member may define a suture channel and a working channel therethrough. A needle passer may extend from a distal end of the elongate member. The needle passer may be pivotally attached to a distal end of the elongate member. A needle grasper may extend from a distal end of the elongate member. The needle passer may be configured to pivot between a first position in which a distal end of the needle passer and a distal end of the needle grasper are separated by a first distance and a second position in which the distal end of the needle passer and the distal end of the needle grasper are separated by a second distance, wherein the first distance is greater than the second distance.

In the above-described and other embodiments, a suture may be movably disposed through the suture channel and a medical accessory device may be movably disposed within the working channel. A distal end of the suture may be attached to a needle. A distal end of the medical accessory device may be configured to extend beyond a distal end of the needle passer and the needle grasper to engage a target tissue.

In yet another aspect, the present disclosure relates to an endoscopic medical device comprising an elongate member. The elongate member may define a suture channel and a working channel therethrough. A suturing arm may extend from a distal end of the elongate member. The distal end of the elongate member may define a first side of a working space. A distal portion of the suturing arm may extend distally of a distal end of the elongate member to define a second side of the working space. The working space may extend between the first and second sides. A needle passer may be movably disposed within a distal portion of the elongate member. The needle passer may be configured to move between a first position on the first side of the working space and a second position on the second side of the working space.

In the above-described and other embodiments, a suture may extend through the suture channel and a medical accessory device may be movably disposed within the working channel. A distal end of the suture may be attached to a needle. A distal end of the medical accessory device may be configured to extend beyond the distal end of the elongate member to engage a target tissue. A needle receiver may be disposed within the portion of the suturing arm extending distally of the distal end of the elongate member.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 5A-5C provide perspective views of an endoscopic medical device, according to one embodiment of the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to single-use endoscopic medical devices with an integrated and purpose-built tissue needle assembly for suturing tissues, it should be appreciated that such endoscopic medical devices may include a variety of end effectors (e.g., scissors, scalpels, clip deployment members, graspers, biopsy needles, injecting needles, staplers, etc.) configured to manipulate tissues in a variety of body lumens, body passageways, organs and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional or physician when introducing a device into a patient, while the term "proximal" refers to the end closest to the medical professional or physician when introducing a device into a patient.

Figure 1A:
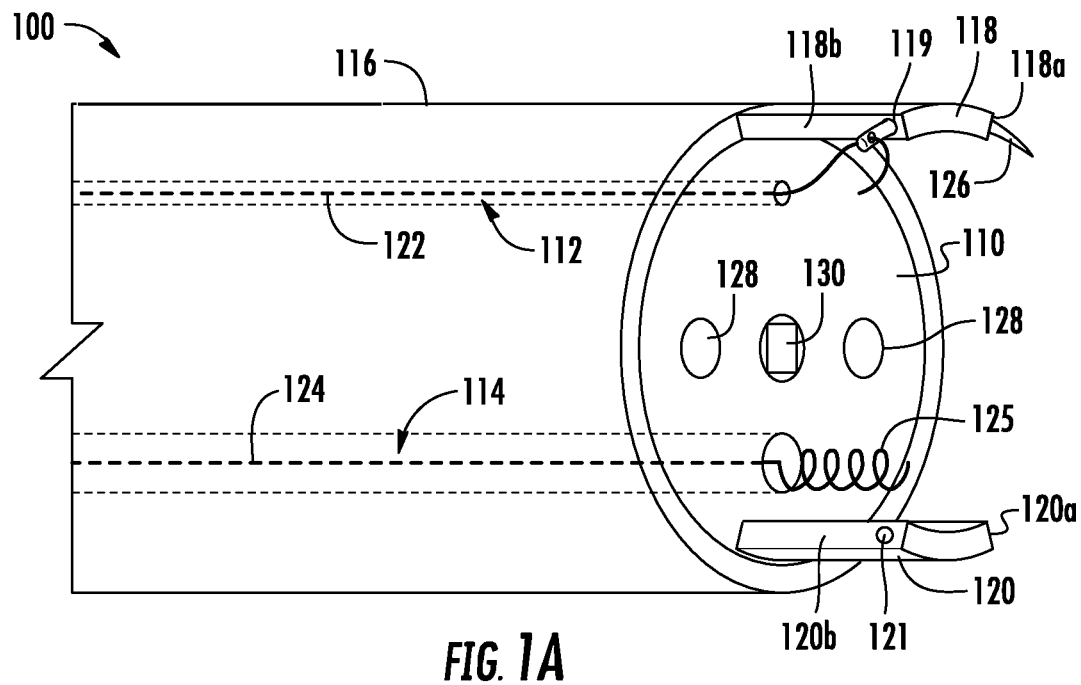
FIGS. 1A-1B provide perspective views of an endoscopic medical device, according to one embodiment of the present disclosure.
Figure 1B:
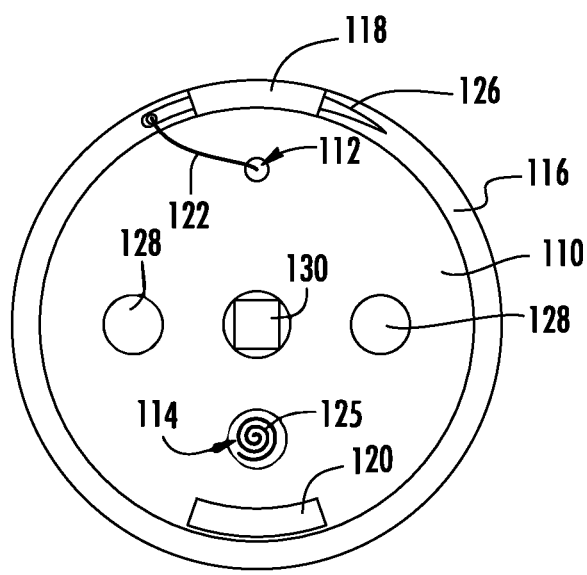

Referring to FIGS. 1A-1B, in one embodiment, a distal end of an endoscopic medical device 100 (e.g., suture device, single-use purpose-built suturing device, etc.) of the present disclosure may include an elongate member 110 (e.g., elongate tubular member, flexible elongate tubular member, endoscope, etc.) and an elongate sheath 116 (e.g., flexible elongate sheath, outer sheath, over-tube, etc.) rotatably disposed about (e.g., around) an outer surface of the elongate member 110. The disclosure pertains to medical devices, e.g., endoscopes, gastroscopes, bronchoscopes, colonoscopes, ureteroscopes, and the like, having integrated features for acquiring, manipulating, and closing openings in target tissue. Although single-use endoscopes are described herein, it is understood that embodiments of the present disclosure may be included in reusable medical devices such as endoscopes as well.

In various embodiments, as discussed below, the elongate sheath 116 may be sufficiently rigid (e.g., include sufficient columnar strength and/or torsional rigidity) that rotational forces exerted on a proximal portion thereof (e.g., a portion of the elongate sheath extending outside a patient) may be efficiently and effectively translated to the distal end of the elongate sheath 116 to support a rotational (e.g., side-to-side, clockwise and counterclockwise) suturing motion within a body passage or lumen. A first channel 112 (e.g., suture channel, dedicated suture channel, etc.) and a second channel 114 (e.g., working channel, dedicated working channel, etc.) may extend through a longitudinal axis of the elongate member 110. A needle passer 118 (e.g., shuttle, etc.) may extend from a distal end of the elongate sheath 116 and a needle grasper 120 may extend from a distal end of the elongate member 110. In various embodiments, the needle passer 118 may be attached to or integrally formed with a distal end of the elongate sheath 116 and the needle grasper 120 may be attached to or integrally formed with a distal end of the elongate member 110. The elongate sheath 116 may be configured to rotate about a full/complete or nearly full/complete outer dimension (e.g., outer circumference) of the elongate member 110 between a first position, a second position and a third position. In the first position, the needle passer 118 may be disposed/positioned substantially opposite the needle grasper 120, e.g., the needle passer 118 and needle grasper 120 may be separated by up to approximately 180 degrees relative to an outer dimension of a distal end of the respective elongate member 110 and elongate sheath 116. In the second position, a first side 118a (e.g., first edge) of the needle passer 118 may be substantially adjacent to (e.g., abutting or in close proximity to) a corresponding first side 120a (e.g., first edge) of the needle grasper 120. In the second position, a second side 118b (e.g., second edge) of the needle passer 118 may be substantially adjacent to (e.g., abutting or in close proximity to) a corresponding second side 120b (e.g., second edge) of the needle grasper 120.

In one embodiment, a suture 122 (e.g., filament, thread, etc.) may extend through the suture channel 112 and a medical accessory device 124 may extend through the working channel 114. A distal end of the suture 122 may be attached to (e.g., glued, tied, etc.) a curved needle 126 releasably attached to the needle passer 118. For example, the curved needle 126 may be releasably housed/held within an aperture 119 extending through the first and second sides 118a, 118b of the needle passer 118. As discussed below, the needle grasper 120 may be configured to receive the curved needle 126 from the needle passer 118 (e.g., when the elongate sheath 116 is rotated in a first direction about the elongate member 110) and to return the curved needle 126 to the needle passer 118 (e.g., when the elongate sheath 116 is rotated in a second direction about the elongate member 110). For example, the curved needle 126 may be releasably received within an aperture 121 extending through the first and second sides 120a, 120b of the needle grasper 120 when the first sides 118a, 120a of the respective needle passer 118 and needle grasper 120 are in the second position. The needle passer 118 may be slightly offset (e.g., bent, angled, etc.), so that the curved needle 126 aligns with the aperture 121 of the needle grasper 120.

In one embodiment, the medical accessory device 124 may be movably (e.g., slidably and/or rotatably, etc.) disposed within the working channel 114 of the elongate member 110 such that a tissue engaging element 125 attached to or integrally formed with a distal end of the medical accessory device 124 may extend beyond a distal end of the elongate member 110. By way of non-limiting example, the tissue engaging element 125 may include a spiral shape (e.g., helical, corkscrew, grasper, etc.) configured to penetrate (e.g., embed, engage, etc.) and reversibly immobilize a portion of a target tissue relative to the distal ends of the elongate member 110 and the elongate sheath 116. The medical accessory device 124, with the tissue engaging element 125 reversibly engaged with the target tissue, may be proximally retracted to pull a portion of the target tissue into a space (e.g., working space) between the needle passer 118 and needle grasper 120, e.g., with the elongate sheath 116 in the first position relative to the elongate member 110. It is understood that the distal end of the medical device 100 may be operable via one or more mechanisms at a proximal end of the medical device, for example, at a handle. A medical professional may articulate the elongate sheath 116, medical accessory device 124, needle passer 118, or needle grasper 120, or combinations thereof, to acquire and suture, or otherwise manipulate tissue via endoscope handle knobs or additional articulation elements.

Figure 2A:
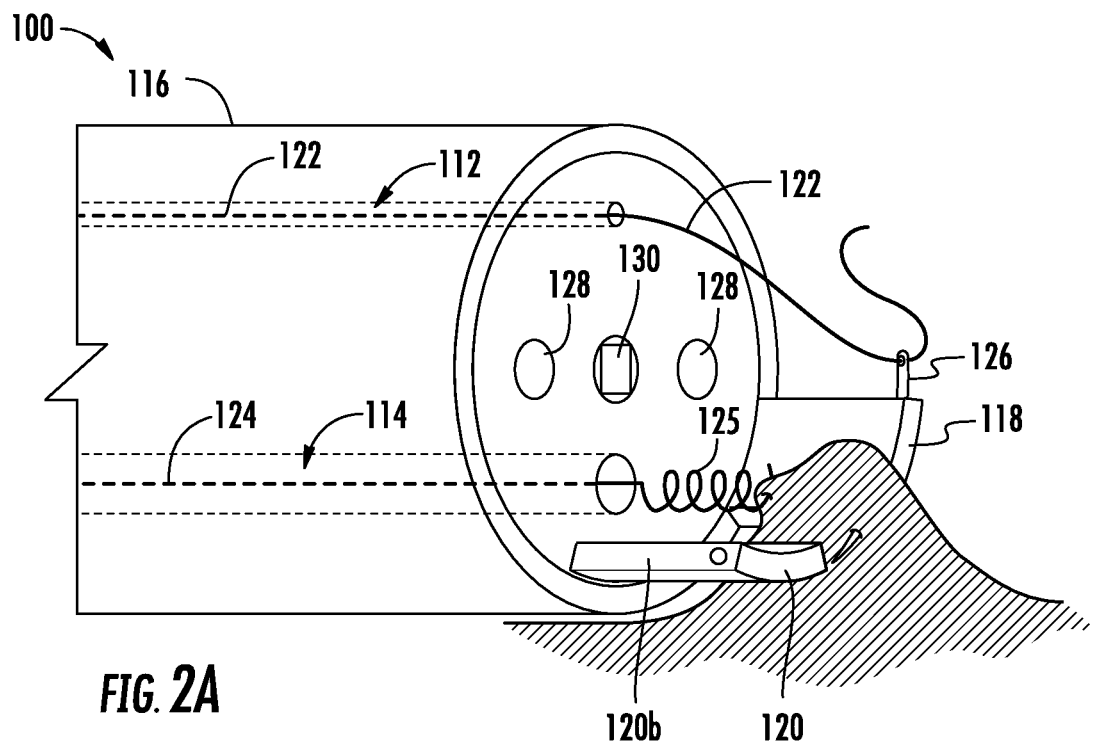
FIGS. 2A-2B provide perspective views of the endoscopic medical device of FIGS. 1A-1B in use, according to one embodiment of the present disclosure.
Figure 2B:
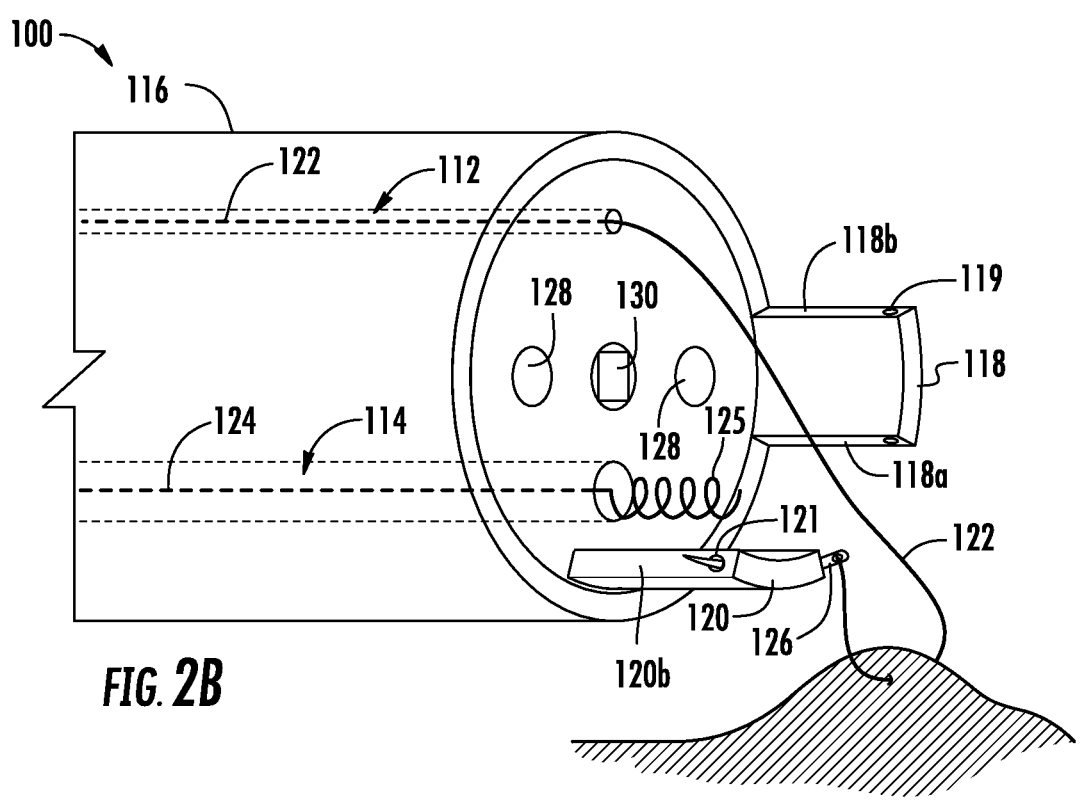

Referring to FIGS. 2A-2B, in use and by way of example, the distal end of an endoscopic medical device 100 of the present disclosure may be advanced through a body lumen or passage and the distal ends of the elongate member 110 and elongate sheath 116 positioned adjacent to a target tissue (e.g., a tissue which may include a portion to be sutured). The medical accessory device 124 may then be distally advanced through the working channel 114 to position the tissue engaging element 125 in contact with a portion of the target tissue. The medical accessory device 124 may then be rotated within the working channel 114 (e.g., in a clockwise or counterclockwise direction) to reversibly embed/engage the tissue engaging element 125 with the target tissue. The medical accessory device 124 may then be proximally retracted within the working channel 114 to pull/draw a portion of the target tissue into the space between the needle passer 118 and the needle grasper 120. The elongate sheath 116 may then be rotated (e.g., by a medical professional rotating a proximal end of the elongate sheath) in a first direction (e.g., clockwise) about the outer surface of the elongate member 110 from the first position to the second position. In various embodiments, as the needle passer 118 moves to the second position (e.g., the first side of the needle passer is adjacent to or substantially abutting or adjacent to the corresponding first side of the needle grasper), a sharpened end of the curved needle 126 and a portion of the suture 122 attached thereto may pass through the target tissue and be received within (e.g., grasped) by the needle grasper (e.g., the curved needle 126 may extend into/through the aperture 121). The elongate sheath 116 may then be rotated in the second direction (e.g., counterclockwise) about the outer surface of the elongate member 110 to return the elongate sheath 116 to the first position, thereby transferring the curved needle 126 to (e.g., releasing the curved needle within) the needle grasper 120. From the first position, the elongate sheath 116 may then be further rotated in the second direction (e.g., counterclockwise) such that the second side of the needle passer 118 is substantially abutting or adjacent to the second side of the needle grasper 120. The sharpened end of the curved needle 126 may be received within (e.g., grasped) by the needle passer 118 (e.g., the curved needle may extend into/through aperture 119), thereby transferring (e.g., releasing, returning) the curved needle 126 to the needle passer 118. The elongate sheath 116 may then be rotated in the first direction (e.g., clockwise) about the outer surface of the elongate member 110 to return to the first position and the tissue engaging element 125 disengaged from the target tissue (e.g., by rotating the medical accessory device in a direction opposite the direction used to engage the target tissue).

In various embodiments, with a first section/length of the suture 122 extending through the target tissue, the distal end of the endoscopic medical device 100 may be repositioned within the body lumen or passage (e.g., proximally retracted or distally advanced) to reposition the needle passer 118 and needle grasper 120 adjacent to a different portion/section of the target tissue. The steps outlined above may then be repeated to suture a second portion of the target tissue. These steps may be performed as many times as necessary to suture (e.g., close) an entire portion/length of the target tissue and the endoscopic medical device 100 removed from within the patient.

In various embodiments, one or more imaging devices, or cameras 128 and one or more illumination devices, or light sources 130 may be disposed on or within the distal end of the elongate member 110 to allow the medical professional to visualize the target tissue and properly manipulate the elongate sheath (e.g., needle passer), elongate member (e.g., needle grasper), curved needle and medical accessory device. It should be appreciated that the peripheral location of the needle passer 118 and needle grasper 120 relative to the respective distal ends of the elongate sheath 116 and elongate member 110 may optimize/maximize visibility of the target tissue as well as the working area within the body lumen or passage. In various embodiments, the elongate member 110 may include one or more additional working channels (not shown) configured to receive additional medical devices, end effectors and/or accessories within the working area. In addition, or alternatively, an elevator (not shown) may be disposed within a distal portion of any of the disclosed working channels to control placement/positioning of the endoscopic medical devices (including the tissue engaging element 125) within the body lumen or passage.

Figure 3A:
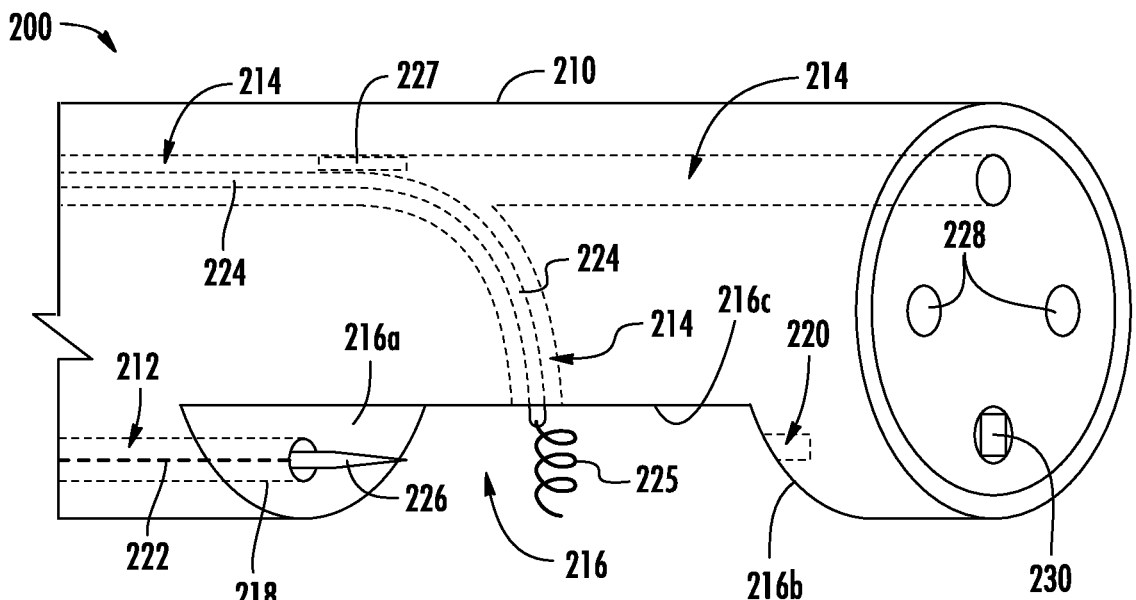
FIGS. 3A-3B provide perspective views of an endoscopic medical device, according to one embodiment of the present disclosure.
Figure 3B:
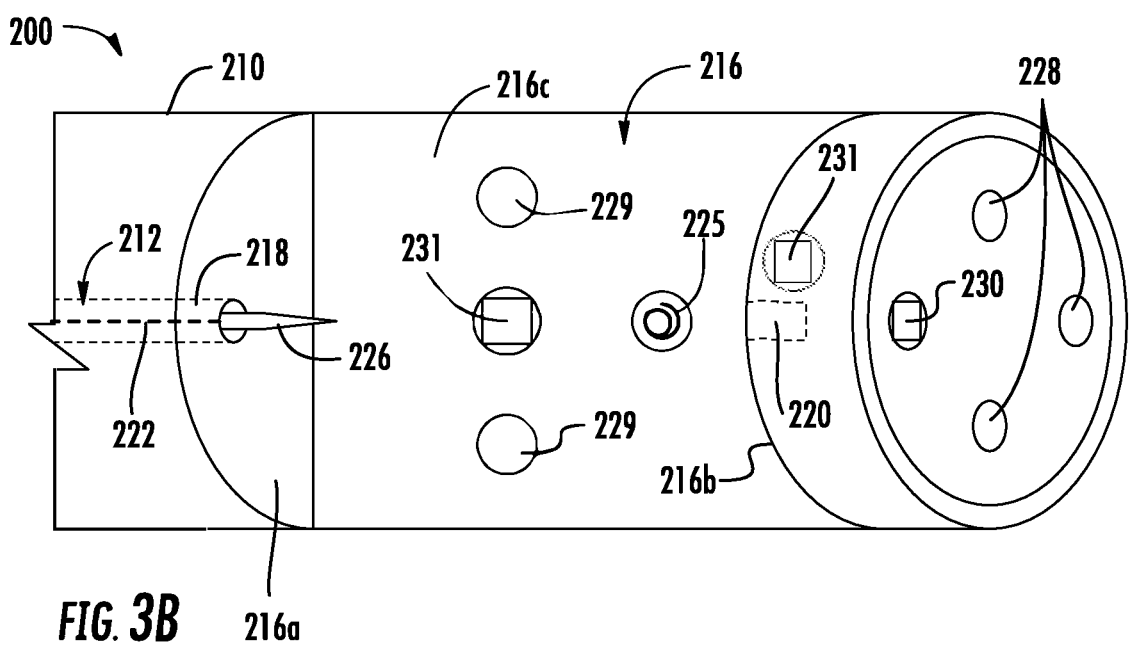

Referring to FIGS. 3A-3B, in one embodiment, a distal end of an endoscopic medical device 200 (e.g., suture device, single-use purpose-built suturing device, etc.) of the present disclosure may include an elongate member 210 (e.g., elongate tubular member, flexible elongate tubular member, endoscope, etc.). A working space 216 (e.g., working area, etc.) may be defined by a distal portion of the elongate member 210, e.g., along one side of a longitudinal axis of the elongate member. In various embodiments, the side of the elongate member 210 within which the working space 216 is formed may be referred to as a "bottom" side of the elongate member 210. The working space 216 may include a first side 216a (e.g., a proximal side defining a proximal surface/wall, etc.), a second side 216b (e.g., a distal side defining a distal surface/wall) and a third side 216c (e.g., a top side defining an upper surface/wall). A first channel 212 (e.g., suture channel, dedicated suture channel, etc.) and a second channel 214 (e.g., working channel, dedicated working channel, etc.) may extend through the elongate member 210, e.g., through the longitudinal axis of the elongate member. A distal end of the first channel 212 may be coextensive with the first side 216a of the working space 216 (e.g., the first channel may open into the working space through the proximal surface/wall) and a distal end of the second channel 214 may be coextensive with the third side 216c of the working space (e.g., the second channel 214 may open into the working space through the upper surface/wall).

A needle passer 218 (e.g., shuttle, etc.) may be movably disposed within the distal portion of the elongate member 210 and configured to move proximally and distally (e.g., back-and-forth) across the working space 216. In various embodiments, the needle passer 218 may be configured to move distally from a first position on the first side 216a of the working space 216 to a second position on the second side 216b of the working space and proximally from the second side 216b of the working space 216 to the first side 216a of the working space 216.

A needle receiver 220 may be disposed on or within the second side 216b (e.g., distal wall) of the working space 216 and configured to receive the needle passer 218, e.g., when the needle passer 218 is in the second position. In various embodiments, the needle receiver 220 may include a slot or recessed portion formed within the second side 216b of the working space 216 and substantially aligned with the opening of the first channel 212, e.g., the slot or recessed portion and the distal end/opening of the first channel 212 may be disposed on substantially opposite sides of the working space 216.

In one embodiment, a suture 222 (e.g., filament, thread, etc.) may extend through the first channel 212 and a medical accessory device 224 may extend through the second channel 214. A distal end of the suture 222 may be attached to (e.g., glued, tied, etc.) a needle 226 engaged by (e.g., attached to) the needle passer 218.

In one embodiment, the medical accessory device 224 may be movably (e.g., slidably and/or rotatably, etc.) disposed within the second channel 214 of the elongate member 210 such that a tissue engaging element 225 (e.g., attached to or integrally formed with a distal end of the medical accessory device 224) may extend into and beyond an opening of the working space 216. By way of non-limiting example, the tissue engaging element 225 may include a spiral (e.g., helical, corkscrew, grasper, etc.) shape configured to penetrate (e.g., embed, engage, etc.) and reversibly immobilize a portion of a target tissue. The medical accessory device 224, with the tissue engaging element 225 reversibly engaged with the target tissue, may be proximally retracted to pull a portion of the target tissue into the working space 216 and between the needle passer 218 and needle receiver 220, e.g., with the needle passer 218 in the first position. It is understood that the distal end of the medical device 200 may be operable via one or more mechanisms at a proximal end of the medical device, for example, at a handle. A medical professional may articulate the elongate member 210, medical accessory device 224, needle passer 218, or needle receiver 220, or combinations thereof, to acquire and suture, or otherwise manipulate tissue via endoscope handle knobs or additional articulation elements.

In use, and by way of example, an endoscopic medical device 200 of the present disclosure may be advanced through a body lumen or passage and the working space 216 positioned adjacent to (e.g., over, above, etc.) a target tissue (e.g., a tissue which may include a portion to be sutured). The medical accessory device 224 may then be distally advanced through the second channel 214 to position the tissue engaging element 225 beyond an opening of the working space 216 and in contact with a portion of the target tissue. The medical accessory device 224 may then be rotated within the second channel 214 (e.g., in a clockwise or counterclockwise direction) to reversibly embed/engage the tissue engaging element 225 with the target tissue. The medical accessory device 224 may then be proximally retracted within the second channel 214 to pull/draw a portion of the target tissue into the working space 216 and between the needle passer 118 (e.g., in the first position) and the needle receiver 220. The needle passer 218, with a needle 226 attached thereto, may then be moved from the first position to the second position such that the needle passer 218 moves distally across the working space 216 and is received within (e.g., extends into) the needle receiver 220. In various embodiments, as the needle passer 218 moves to the second position, a sharpened end of the needle 226 and a portion of the suture 222 attached thereto may pass through the target tissue immobilized by the tissue engaging element 225 within the working space 216. The tissue engaging element 225 may then be disengaged from the target tissue (e.g., by rotating the medical accessory device in a direction opposite the direction used to engage the target tissue). The needle passer 218, with the needle 226 attached thereto, may then be moved from the second position to the first position such that the needle passer 218 moves proximally across the working space 216 and returns to the first position, e.g., the initial/starting position.

In various embodiments, with a first section/length of the suture 222 extending through the target tissue, the endoscopic medical device 200 may be repositioned within the body lumen or passage (e.g., proximally retracted or distally advanced) to position the working space 216 adjacent to a different portion/section of the target tissue. The steps outlined above may then be repeated to suture a second portion of the target tissue. These steps may be performed as many times as necessary to suture (e.g., close) an entire portion of the target tissue and the endoscopic medical device 200 removed from within the patient.

Referring again to FIG. 3A, in one embodiment, the second channel 214 may include a first portion (e.g., first branch) which extends into the working space 216 (as discussed above) and a second portion (e.g., second branch) that extends through the remaining longitudinal portion of the elongate member 210, e.g., such that an opening of the second portion of the second channel is coextensive with a distal end of the elongate member 210. In various embodiments, an elevator 227 may be disposed at or near a junction of the first and second portions of the second channel 214. A medical professional may move/actuate the elevator 227 as necessary to direct the medical accessory device 224 through the desired portion of the second channel 214. For example, the elevator 227 may be moved to a first position in which the second portion of the second channel 214 remains accessible (e.g., not blocked or obstructed) to allow the medical accessory device 224 to extend beyond the distal end of the elongate member 210, e.g., to examine or manipulate a target tissue beyond a distal end of the endoscopic medical device 200. Alternatively, the elevator 227 may move to a second position within the second channel 214 to direct/deflect the medical accessory device 224 into the working space 216 (as discussed above). As above, in addition to directing the medical accessory device 224 through the desired portion of the second channel 214, the elevator 227 may control placement/positioning of the medical accessory device (including the tissue engaging element 225) within the working space 216 and/or beyond an opening of the working space 216.

In various embodiments, one or more imaging devices, or cameras 228 and one or more illumination devices, or light sources 230 may be disposed on or within the distal end of the elongate member 210 to allow the medical professional to visualize the body lumen and/or target tissue, e.g., to navigate through the body lumen and/or properly position the working space 216 relative to the target tissue. In various additional embodiments, one or more additional cameras 229 and one or more additional light sources 231 may be disposed on or within the second side 216b or third side 216c (e.g., upper surface) of the working space 216 and/or adjacent to the needle receiver 220, e.g., to properly position the working space relative to the target tissue and manipulate the target tissue. It should be appreciated that the peripheral location the needle passer 218 and needle receiver 220 on the first and second sides of the working space 216 may optimize/maximize visibility of the target tissue within the working space. In various additional embodiments, the elongate member 210 may include one or more additional working channels (not shown) configured to receive additional medical devices, end effectors and/or accessories into the working space 216 and/or beyond the distal end of the elongate member 210.

Figure 4A:
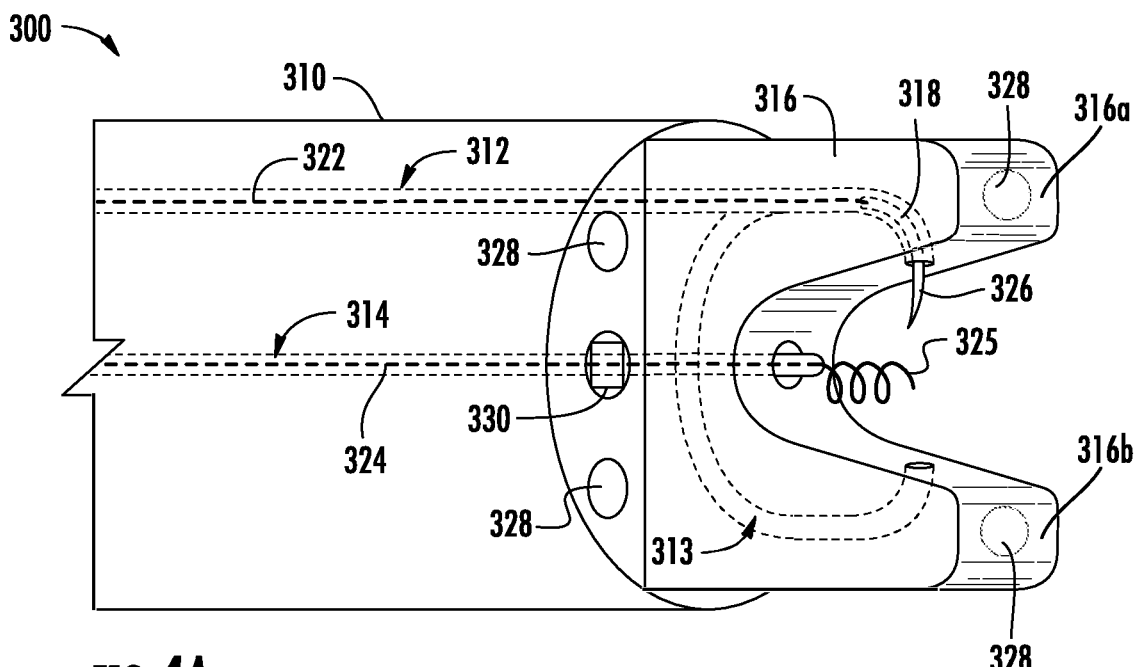
FIGS. 4A-4B provide perspective views of an endoscopic medical device, according to one embodiment of the present disclosure.
Figure 4B:
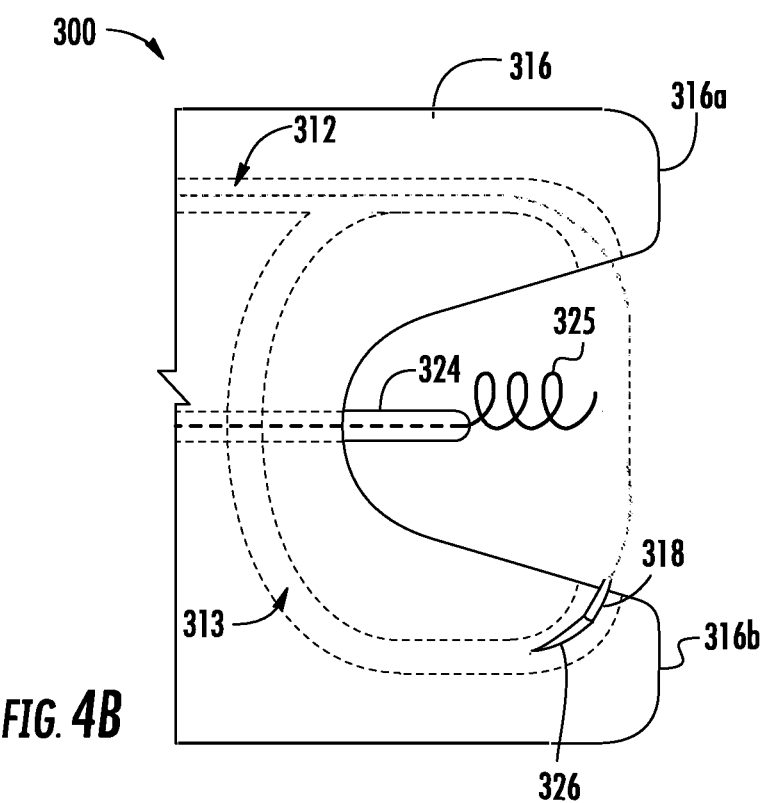

Referring to FIGS. 4A-4B, in one embodiment, an endoscopic medical device 300 (e.g., suture device, single-use purpose-built suturing device, etc.) of the present disclosure may include an elongate member 310 (e.g., elongate tubular member, flexible elongate tubular member, endoscope, etc.). A suturing arm 316 may extend from a distal end of the elongate member 310. In various embodiments, the suturing arm 316 may be attached to or integrally formed with a distal end of the elongate member 310. The suturing arm 316 may include first and second projections 316a, 316b (e.g., first and second fingers or tabs) defining a space or opening (e.g., working space, etc.) therebetween. A first channel 312 (e.g., suture channel, dedicated suture channel, etc.) may extend through a longitudinal axis of the elongate member and through the first projection 316a of the suturing arm 316. A second channel 314 (e.g., working channel, dedicated working channel, etc.) may extend through the longitudinal axis of the elongate member 310 and through a portion of the suturing arm 316 between the first and second projections 316a, 316b. A distal end of the first channel 312 may be coextensive with (e.g., open into) a first side of the working space (e.g., the suture channel may open into the working space through an end of the first projection 316a) and a distal end of the second channel 314 may be coextensive with (e.g., open into) the working space between the first and second projections 316a, 316b.

A curved needle passer 318 (e.g., shuttle, etc.) may be movably disposed within a third channel 313 of the suturing arm 316 and configured to move along a 360-degree path (e.g., rotate, revolve, etc.) within the suturing arm 316. In various embodiments, the curved needle passer 318 may be configured to move along the curved path from a first position (e.g., housed within the first projection 316a), across or through the working space between the first and second projections 316a, 316b, to a second position (e.g., housed within the second projection 316b).

In one embodiment, a suture 322 (e.g., filament, thread, etc.) may extend through the first channel 312 and a medical accessory device 324 may extend through the second channel 314. A distal end of the suture 322 may be attached to (e.g., glued, tied, etc.) a curved needle 326 attached to the curved needle passer 318.

In one embodiment, the medical accessory device 324 may be movably (e.g., slidably and/or rotatably, etc.) disposed within the second channel 314 of the elongate member 310 and suturing arm 316 such that a tissue engaging element 325 attached to or integrally formed with a distal end of the medical accessory device 324 may extend beyond a distal end of the suturing arm 316. By way of non-limiting example, the tissue engaging element 325 may include a spiral (e.g., helical, corkscrew, grasper, etc.) shape configured to penetrate (e.g., embed, engage, etc.) a target tissue and reversibly immobilize a portion of a target tissue relative to a distal end of the suturing arm 316. The medical accessory device 324, with the tissue engaging element 325 reversibly engaged with the target tissue, may be proximally retracted to pull a portion of the target tissue into the working space between the first and second projections 316a, 316b of the suturing arm 316. It is understood that the distal end of the medical device 300 may be operable via one or more mechanisms at a proximal end of the medical device, for example, at a handle. A medical professional may articulate the elongate member 310, medical accessory device 324 or needle passer 318, or combinations thereof, to acquire and suture, or otherwise manipulate tissue via endoscope handle knobs or additional articulation elements.

In use and by way of example, an endoscopic medical device 300 of the present disclosure may be advanced through a body lumen or passage and the distal ends of the first and second projections 316a, 316b of the suturing arm 316 positioned adjacent to a target tissue (e.g., a tissue which may include a portion to be sutured). The medical accessory device 324 may then be distally advanced through the second channel 314, and through the working space defined by the first and second projections 316a, 316b, to position the tissue engaging element 325 in contact with a portion of the target tissue beyond a distal end of the suturing arm 316. The medical accessory device 324 may then be rotated within the second channel (e.g., in a clockwise or counter-clockwise direction) to reversibly embed/engage the tissue engaging element 325 with the target tissue. The medical accessory device 324 may then be proximally retracted within the second channel 314 to pull/draw a portion of the target tissue into the working space between the first and second projections 316a, 316b. The curved needle passer 318, with a curved needle 326 attached thereto, may then be moved (e.g., rotated) along a curved path from a first position housed within the first projection 316a, across/through the working space between the first and second projection 316a, 316b, to a second position housed within the second projection 316b. In various embodiments, as the curved needle passer 318 moves to the second position, a sharpened end of the curved needle 326 and a portion of the suture 322 attached thereto may pass through the target tissue immobilized by the tissue engaging element 325 within the working space. The tissue engaging element 325 may then be disengaged from the target tissue (e.g., by rotating the medical accessory device in a direction opposite the direction used to engage the target tissue). The curved needle passer 318, and curved needle 326 attached thereto, may then be further moved (e.g., rotated, revolved, etc.) through third channel 313 of the suturing arm 316 to return to the first position (e.g., initial/starting position) housed within the first projection 316a.

In various embodiments, with a first section/length of the suture 322 extending through the target tissue, the endoscopic medical device 300 may be repositioned within the body lumen or passage (e.g., proximally retracted or distally advanced) to position the first and second projections 316a, 316b of the suturing arm 316 adjacent to a different portion/section of the target tissue. The steps outlined above may then be repeated to suture a second portion of the target tissue. These steps may be performed as many times as necessary to suture (e.g., close) an entire portion of the target tissue and the endoscopic medical device 300 removed from within the patient.

In various embodiments, one or more imaging devices, or cameras 328 and one or more illumination devices, or light sources 330 may be disposed on or within the distal end of the elongate member 310, and/or the distal ends of the first and second projections 316a, 316b of the suturing arm 316, to allow the medical professional to visualize the target tissue and properly manipulate the curved needle passer 318 and medical accessory device 324. In various embodiments, the elongate member 310 and/or suturing arm 316 may include one or more additional working channels (not shown) configured to receive additional medical devices, end effectors and/or accessories beyond the distal end of thereof. In addition, or alternatively, an elevator (not shown) may be disposed within a distal portion of any of the disclosed working channels to control placement/positioning of the endoscopic medical devices (including the tissue engaging element 325) within the body lumen or passage.

Referring to FIGS. 5A-5C, in one embodiment, a distal end of an endoscopic medical device 400 (e.g., suture device, single-use purpose-built suturing device, etc.) of the present disclosure may include an elongate member 410 (e.g., elongate tubular member, flexible elongate tubular member, endoscope, etc.). A needle passer 418 (e.g., shuttle, etc.) and a needle grasper 420 may extend from a distal end of the elongate member 410. A first channel 412 (e.g., suture channel, dedicated suture channel, etc.) and a second channel 414 (e.g., working channel, dedicated working channel, etc.) may extend through a longitudinal axis of the elongate member 410. The first channel 412 may extend along one side of the elongate member 410 such that a distal end of the first channel 412 may be coextensive with (e.g., open into) a distal end of the elongate member 410 adjacent to (e.g., above) the needle passer 418. The second channel 414 may extend along a central portion of the elongate member 410 such that a distal end of the second channel 414 may be coextensive with (e.g., open into) the distal end of the elongate member between 410 the needle passer 418 and the needle grasper 420. In various embodiments, the needle passer 418 may be pivotally attached to the distal end of the elongate member 410 and the needle grasper 420 may be fixedly (e.g., immovably) attached to or integrally formed with the distal end of the elongate member 410. The needle passer 418 may be configured to move (e.g., pivot back-and-forth) between a first position (FIG. 5B) and a second position (FIG. 5C) relative to the stationary needle grasper 420. For example, in the first position, the needle grasper 420 may extend from the distal end of the elongate member 410 substantially parallel to a longitudinal axis of the elongate member 410, and the needle passer 418 may be disposed at an angle relative to the longitudinal axis of the elongate member 410 and/or the needle grasper 420. In the second position, the needle passer 418 may extend from the distal end of the elongate member 410 substantially parallel to a longitudinal axis of the elongate member 410 and parallel to (e.g., alongside) the needle grasper 420. In the first position a distal end of the needle passer 418 may be separated from a distal end of the needle grasper 420 by a first distance and in the second position the distal end of the needle passer 418 may be separated from the distal end of the needle grasper 420 by a second distance, the second distance being less than the first distance.

Alternatively, in one embodiment, both the needle passer 418 and the needle grasper 420 may be pivotally attached to the distal end of the elongate member 410 and configured to move (e.g., pivot back-and-forth) between a first position and a second position. For example, in the first position, the needle grasper 420 and the needle passer 418 may be disposed at an angle relative to the longitudinal axis of the elongate member 410. In the second position, the needle passer 418 and needle grasper 420 may extend from the distal end of the elongate member 410 substantially parallel to a longitudinal axis of the elongate member 410 and parallel to (e.g., alongside) to each other. In the first position a distal end of the needle passer 418 may be separated from a distal end of the needle grasper 420 by a first distance and in the second position the distal end of the needle passer 418 may be separated from the distal end of the needle grasper 420 by a second distance, the second distance being less than the first distance.

In one embodiment, a suture 422 (e.g., filament, thread, etc.) may extend through the first channel 412 and a medical accessory device 424 may extend through the second channel 414. A distal end of the suture 422 may be attached to (e.g., glued, tied, etc.) a needle 426 releasably attached to the needle passer 418. For example, the needle 426 may be releasably held/maintained within an aperture 419 extending through the needle passer 418. As discussed below, the needle grasper 420 may be configured to receive the needle 426 from the needle passer 418 (e.g., within an aperture 421 extending through the needle grasper 420) following a first actuation (e.g., when the needle passer 418 moves/pivots from the first position to the second position a first time) and return the needle to 426 to the needle passer 418 following a second actuation (e.g., when the needle passer 418 moves/pivot from the first to second position a second/subsequent time).

In one embodiment, the medical accessory device 424 may be movably (e.g., slidably and/or rotatably, etc.) disposed within the second channel 414 of the elongate member such that a tissue engaging element 425 attached to or integrally formed with a distal end of the medical accessory device 424 may extend beyond a distal end of the elongate member 410 between the needle passer 418 and needle grasper 420. By way of non-limiting example, the tissue engaging element 425 may include a spiral (e.g., helical, corkscrew, grasper, etc.) shape configured to penetrate (e.g., embed, engage, etc.) a target tissue and reversibly immobilize a portion of a target tissue relative to the distal end of the elongate member 410. The medical accessory device 424, with the tissue engaging element 425 reversibly engaged with the target tissue, may be proximally retracted to pull a portion of the target tissue into a space (e.g., working space) between the needle passer 418 and needle grasper 420, e.g., with the needle passer 418 in the first position relative to the needle grasper 420.

In use and by way of example, an endoscopic medical device 400 of the present disclosure may be advanced through a body lumen or passage and the distal ends of the needle passer 418 and needle grasper 420 positioned adjacent to a target tissue (e.g., a tissue which may include a portion to be sutured). The medical accessory device 424 may then be distally advanced through the second channel 414, and through the working space between the needle passer 418 and needle grasper 420, to position the tissue engaging element 425 in contact with a portion of the target tissue beyond a distal end of the needle passer 418 and needle grasper 420. The medical accessory device 424 may then be rotated within the second channel (e.g., in a clockwise or counterclockwise direction) to reversibly embed/engage the tissue engaging element 425 with the target tissue. The medical accessory device 424 may then be proximally retracted within the second channel 414 to pull/draw a portion of the target tissue into the working space between the needle passer 416 and the needle grasper 420. The needle passer 418, with a needle 426 releasably attached thereto (e.g., extending perpendicular to the needle passer), may then be moved (e.g., pivoted) from the first position to the second position and the needle released from the needle passer 418 and transferred to the needle grasper 420. In various embodiments, as the needle passer 418 moves to the second position, a sharpened end of the needle 426 and a portion of the suture 422 attached thereto may pass through the target tissue immobilized by the tissue engaging element 425 between the needle passer 418 and needle grasper. The needle passer 418 may then move from the second position to the first position and the tissue engaging element 425 may be disengaged from the target tissue (e.g., by rotating the medical accessory device in a direction opposite the direction used to engage the target tissue). The needle passer 418 may then be moved (e.g., pivoted) from the first position to the second position to transfer (e.g., return) the needle 426 from the needle grasper 420 back to the needle passer 418. The needle passer 418, with the needle 426 releasably attached thereto, may then be moved from the second position to the first position.

In various embodiments, with a first section/length of the suture 422 extending through the target tissue, and the needle passer 418 returned to the first position, the endoscopic medical device 400 may be repositioned within the body lumen or passage (e.g., proximally retracted or distally advanced) to position the distal ends of the needle passer 418 and needle grasper 420 adjacent to a different portion/section of the target tissue. The steps outlined above may then be repeated to suture a second portion of the target tissue. These steps may be performed as many times as necessary to suture (e.g., close) an entire portion of the target tissue and the endoscopic medical device 400 removed from within the patient.

In various embodiments, one or more imaging devices, or cameras 428 and one or more illumination devices, or light sources 430 may be disposed on or within the distal end of the elongate member 410 to allow the medical professional to visualize the target tissue and properly manipulate the needle passer 418 and medical accessory device 424. In various embodiments, the elongate member 410 may include one or more additional working channels (not shown) configured to receive additional medical devices, end effectors and/or accessories beyond the distal end of thereof. In addition, or alternatively, an elevator (not shown) may be disposed within a distal portion of any of the disclosed working channels to control placement/positioning of the endoscopic medical devices (including the tissue engaging element 425) within the body lumen or passage.

Figure 6A:
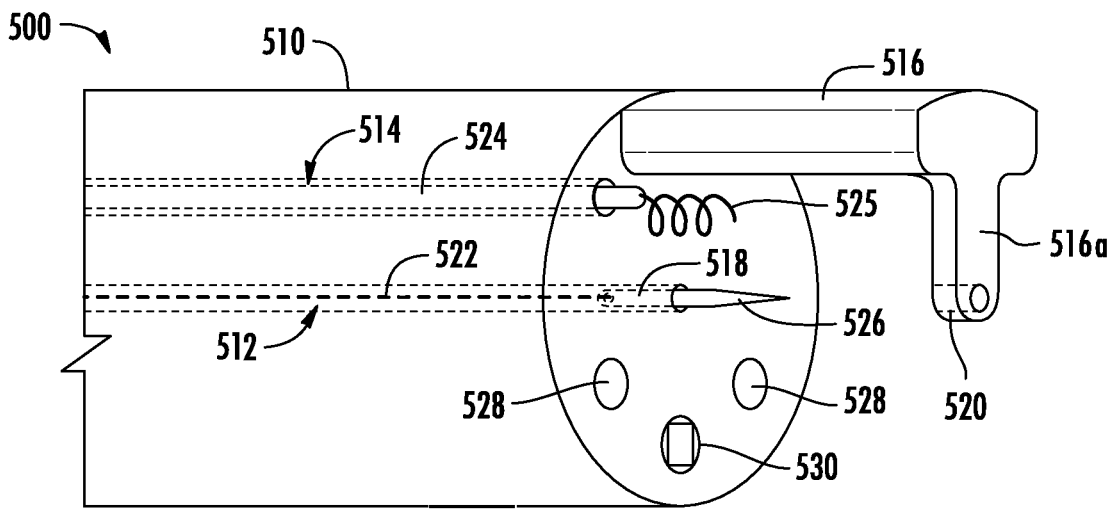
FIGS. 6A-6C provide perspective views of an endoscopic medical device, according to one embodiment of the present disclosure.
Figure 6B:
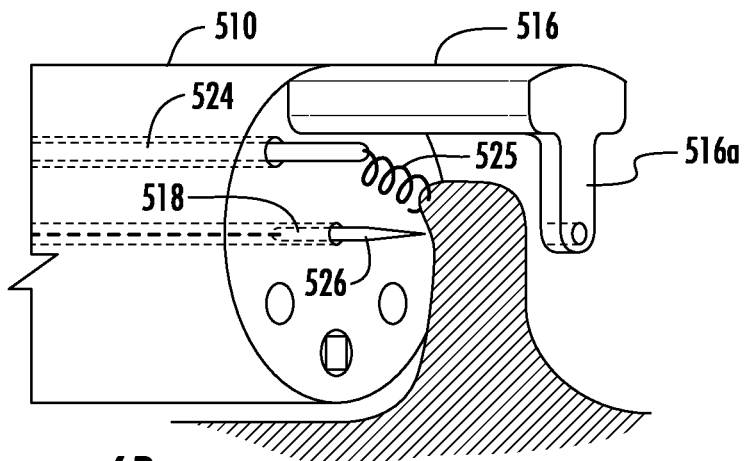
Figure 6C:
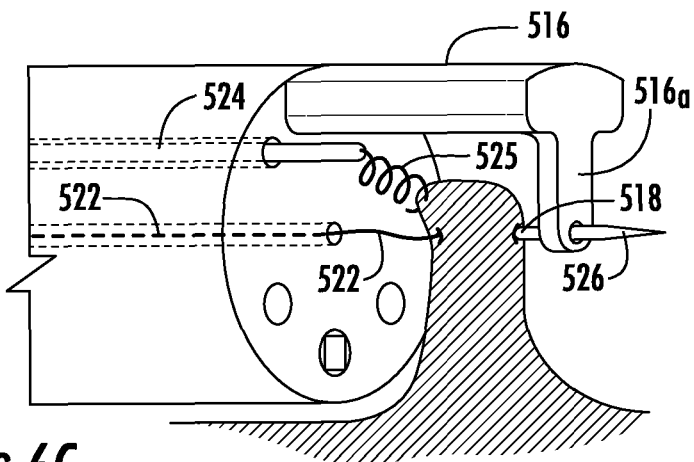

Referring to FIGS. 6A-6C, in one embodiment, a distal end of an endoscopic medical device 500 (e.g., suture device, single-use purpose-built suturing device, etc.) of the present disclosure may include an elongate member 510 (e.g., elongate tubular member, flexible elongate tubular member, endoscope, etc.). A suturing arm 516 may extend from a distal end of the elongate member 510. A distal portion 516a of the suturing arm 516 may extend distally beyond (e.g., in front of) a distal end of the elongate member 510 to define a working space therebetween (e.g., a working space between the distal end of the elongate member 510 and a proximal surface of the distal portion 516a of the suturing arm 516). A first channel 512 (e.g., suture channel, dedicated suture channel, etc.) and a second channel 514 (e.g., working channel, dedicated working channel, etc.) may extend through a longitudinal axis of the elongate member 510. A distal end of the suture channel 512 and a distal end of the working channel 514 may be coextensive with the working space (e.g., the suture channel 512 and working channel 514 may open into the working space at the distal end of the elongate member 510).

A needle passer 518 (e.g., shuttle, etc.) may be movably disposed within the distal portion of the elongate member 510 and configured to move proximally and distally (e.g., back-and-forth) across the working space (e.g., between the distal end of the elongate member 510 and the proximal surface of the distal portion 516a of the suturing arm 516). In various embodiments, the needle passer 518 may be configured to move distally from a first position on a first side of the working space to a second position on a second side of the working space and proximally from the second side of the working space to the first side of the working space.

A needle receiver 520 may be disposed on or within the distal portion 516a of the suturing arm 516 and configured to receive the needle passer 518, e.g., when the needle passer 518 is in the second position. In various embodiments, the needle receiver 520 may include a slot or recessed portion formed within the proximal surface of the distal portion 516 and substantially aligned with the opening of the suture channel 512, e.g., the slot or recessed portion and the distal end/opening of the suture channel 512 may be disposed on substantially opposite sides of the working space.

In one embodiment, a suture 522 (e.g., filament, thread, etc.) may extend through the suture channel 512 and a medical accessory device 524 may extend through the working channel 514. A distal end of the suture 522 may be attached to (e.g., glued, tied, etc.) a needle 526 engaged by (e.g., attached to) the needle passer 518.

In one embodiment, the medical accessory device 524 may be movably (e.g., slidably and/or rotatably, etc.) disposed within the working channel 514 of the elongate member 510 such that a tissue engaging element 525 (e.g., attached to or integrally formed with a distal end of the medical accessory device 524) may extend into and beyond an opening of the working space. By way of non-limiting example, the tissue engaging element 525 may include a spiral (e.g., helical, corkscrew, grasper, etc.) shape configured to penetrate (e.g., embed, engage, etc.) and reversibly immobilize a portion of a target tissue. The medical accessory device 524, with the tissue engaging element 525 reversibly engaged with the target tissue, may be proximally retracted to pull a portion of the target tissue into the working space and between the needle passer 518 and the distal portion 516a of the suturing arm 56, e.g., with the needle passer 518 in the first position.

In use, and by way of example, a distal end of an endoscopic medical device 500 of the present disclosure may be advanced through a body lumen or passage and the working space positioned adjacent to (e.g., over, above, etc.) a target tissue (e.g., a tissue which may include a portion to be sutured). The medical accessory device 524 may then be distally advanced through the working channel 514 to position the tissue engaging element 525 beyond an opening of the working space and in contact with a portion of the target tissue. The medical accessory device 524 may then be rotated within the working channel 514 (e.g., in a clockwise or counterclockwise direction) to reversibly embed/engage the tissue engaging element 525 with the target tissue. The medical accessory device 524 may then be proximally retracted within the working channel 514 to pull/draw a portion of the target tissue into the working space and between the needle passer 518 (e.g., in the first position) and the distal portion 516a of the suturing arm 516. The needle passer 518, with a needle 526 attached thereto, may then be moved from the first position to the second position such that the needle passer 518 moves distally across the working space and is received within (e.g., extends into) the needle receiver 520 of the distal portion 516a of the suturing arm 516. In various embodiments, as the needle passer 518 moves to the second position, a sharpened end of the needle 526 and a portion of the suture 522 attached thereto may pass through the target tissue immobilized by the tissue engaging element 525 within the working space. The tissue engaging element 525 may then be disengaged from the target tissue (e.g., by rotating the medical accessory device in a direction opposite the direction used to engage the target tissue). The needle passer 518, with the needle 526 attached thereto, may then be moved from the second position to the first position such that the needle passer 518 moves proximally across the working space and returns to the first position, e.g., the initial/starting position.

In various embodiments, with a first section/length of the suture 522 extending through the target tissue, the endoscopic medical device 500 may be repositioned within the body lumen or passage (e.g., proximally retracted or distally advanced) to position the working space adjacent to a different portion/section of the target tissue. The steps outlined above may then be repeated to suture a second portion of the target tissue. These steps may be performed as many times as necessary to suture (e.g., close) an entire portion of the target tissue and the endoscopic medical device 500 removed from within the patient.

In various embodiments, the endoscopic medical devices 100, 200, 300, 400, 500 which may be single-use and include integrated and purpose-built functionality, may provide a variety of advantages as compared to reusable multipurpose endoscopes. For example, the single-use endoscopic medical devices 100, 200, 300, 400, 500 may mitigate the risk of patient infection associated with more complex reusable endoscopes and associated medical tools, which require sterilization between each use. In addition, the built-in functionality may allow for the disclosed endoscopic medical devices 100, 200, 300, 400, 500 to be smaller and more maneuverable than reusable endoscopes, which must accommodate a wide range of medical devices for a variety of different/unrelated medical procedures.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
   an endoscope, wherein the endoscope defines a suture channel and a working channel therethrough;
   an elongate sheath rotatably disposed about the endoscope, the elongated sheath including a lumen, wherein the endoscope is disposed within the lumen of the elongated sheath;
   a needle passer extending from a distal end of the elongate sheath; and
   a needle grasper extending from a distal end of the endoscope;
   wherein the elongate sheath is configured to rotate about the endoscope between a first position, a second position and a third position;
   wherein, in the first position, the needle passer is disposed substantially opposite the needle grasper;
   wherein, in the second position, a first side of the needle passer is substantially adjacent to a first side of the needle grasper; and
   wherein, in the third position, a second side of the needle passer is substantially adjacent to a second side of the needle grasper.

2. The medical device of claim 1, further comprising a suture movably disposed within the suture channel and a medical accessory device movably disposed within the working channel.

3. The medical device of claim 2, wherein a distal end of the suture is attached to a curved needle.

4. The medical device of claim 3, wherein in the first position the curved needle is releasably attached to the needle passer;
   wherein in the second position the curved needle is transferred from the needle passer to the needle grasper; and
   wherein in the third position the curved needle is transferred from the needle grasper to the needle passer.

5. The medical device of claim 2, wherein a distal end of the medical accessory device is configured to extend beyond the distal end of the endoscope to engage a target tissue.

6. The medical device of claim 1, further comprising a camera disposed on the distal end of the elongate member.

7. The medical device of claim 1, further comprising a light source disposed on the distal end of the elongate member.

* * * * *